(12) United States Patent
Shores et al.

(10) Patent No.: US 7,549,992 B2
(45) Date of Patent: Jun. 23, 2009

(54) SURGICAL INSTRUMENT WITH ANGLED ATTACHMENT

(75) Inventors: Rex Wesley Shores, Norfolk, MA (US); Larry D. Estes, North Richland Hills, TX (US); Paul A. Cihak, Grapevine, TX (US); Allen P. Hilton, Arlington, TX (US); Donald L. Hilton, Jr., San Antonio, TX (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 10/698,177

(22) Filed: Oct. 31, 2003

(65) Prior Publication Data

US 2006/0178672 A1 Aug. 10, 2006

Related U.S. Application Data

(63) Continuation-in-part of application No. 10/326,178, filed on Dec. 20, 2002.

(51) Int. Cl.
 *A61B 17/00* (2006.01)
(52) U.S. Cl. .......................................... 606/79; 606/80
(58) Field of Classification Search .............. 606/79–85
 See application file for complete search history.

(56) References Cited

U.S. PATENT DOCUMENTS

| | | | |
|---|---|---|---|
| 2,807,473 A | | 9/1957 | Kiehne |
| 3,835,858 A | | 9/1974 | Hagen |
| 4,203,222 A | | 5/1980 | Matchen |
| 4,265,231 A | * | 5/1981 | Scheller et al. ............... 606/80 |
| 4,298,074 A | * | 11/1981 | Mattchen .................... 173/129 |
| 4,699,550 A | | 10/1987 | Baker |
| 4,728,876 A | * | 3/1988 | Mongeon et al. ............ 320/114 |
| 4,751,922 A | * | 6/1988 | DiPietropolo ................ 606/80 |
| 5,152,744 A | * | 10/1992 | Krause et al. ................. 604/22 |
| 5,222,956 A | | 6/1993 | Waldron |
| 5,320,635 A | * | 6/1994 | Smith ......................... 606/180 |
| 5,330,480 A | | 7/1994 | Meloul et al. |
| 5,340,129 A | * | 8/1994 | Wright ......................... 279/90 |
| 5,347,988 A | | 9/1994 | Hori |
| 5,380,333 A | | 1/1995 | Meloul et al. |

(Continued)

FOREIGN PATENT DOCUMENTS

WO 02/076308 10/2002

OTHER PUBLICATIONS

Medtronic Brochure, "Midas Rex Classic Dissecting Tool Guide", Printed in USA, 2000.

(Continued)

*Primary Examiner*—Eduardo C Robert
*Assistant Examiner*—Jerry Cumberledge
(74) *Attorney, Agent, or Firm*—Haynes and Boone LLP

(57) ABSTRACT

In one embodiment, there is disclosed a surgical instrument for the dissection of bone or other tissue, the surgical instrument including a tool having a shaft with a dissection area disposed adjacent a distal end and a coupling area disposed adjacent a proximal end; a coupling assembly configured for coupling to a power output of a motor to said coupling area of said tool; and an angled attachment tube positionable along at least a portion of said shaft and substantially supporting a portion of said shaft disposed adjacent said dissection area.

18 Claims, 7 Drawing Sheets

U.S. PATENT DOCUMENTS

| | | | |
|---|---|---|---|
| 5,439,005 A | 8/1995 | Vaughn | |
| 5,490,683 A | 2/1996 | Mickel et al. | |
| 5,505,737 A | 4/1996 | Gosselin et al. | |
| 5,529,580 A * | 6/1996 | Kusunoki et al. | 606/170 |
| 5,569,256 A * | 10/1996 | Vaughn et al. | 606/80 |
| 5,593,416 A * | 1/1997 | Donahue | 606/170 |
| 5,601,560 A | 2/1997 | Del Rio et al. | |
| 5,630,818 A | 5/1997 | Del Rio et al. | |
| 5,741,263 A | 4/1998 | Umber et al. | |
| 5,779,404 A | 7/1998 | Jore | |
| 5,782,836 A | 7/1998 | Umber et al. | |
| 5,833,704 A | 11/1998 | McCombs et al. | |
| 5,851,208 A * | 12/1998 | Trott | 606/80 |
| 5,888,200 A | 3/1999 | Walen | |
| 5,893,851 A | 4/1999 | Umber et al. | |
| 5,904,687 A | 5/1999 | Del Rio et al. | |
| 5,913,859 A * | 6/1999 | Shapira | 606/80 |
| 5,922,003 A * | 7/1999 | Anctil et al. | 606/170 |
| 5,928,238 A | 7/1999 | Scarborough et al. | |
| 5,928,241 A | 7/1999 | Menut et al. | |
| 5,941,891 A | 8/1999 | Walen | |
| 5,989,257 A * | 11/1999 | Tidwell et al. | 606/79 |
| 5,993,453 A | 11/1999 | Bullara et al. | |
| 5,993,454 A | 11/1999 | Longo | |
| 6,033,408 A | 3/2000 | Gage et al. | |
| 6,062,575 A | 5/2000 | Mickel et al. | |
| 6,209,886 B1 | 4/2001 | Estes et al. | |
| 6,270,087 B1 | 8/2001 | Mickel et al. | |
| RE37,358 E | 9/2001 | Del Rio et al. | |
| 6,312,438 B1 | 11/2001 | Adams | |
| 6,423,070 B1 * | 7/2002 | Zeppelin | 606/79 |
| 6,457,916 B2 | 10/2002 | Weinhold | |
| 6,562,055 B2 | 5/2003 | Walen | |
| 6,616,149 B1 | 9/2003 | Pjevach et al. | |
| 6,733,218 B2 * | 5/2004 | Del Rio et al. | 409/231 |
| 7,001,391 B2 | 2/2006 | Estes et al. | |
| 2004/0122460 A1 | 6/2004 | Shores et al. | |
| 2006/0178672 A1 | 8/2006 | Shores et al. | |

OTHER PUBLICATIONS

Medtronic Brochure, "Midas Rex Classic System", Printed in USA, 2000.

* cited by examiner

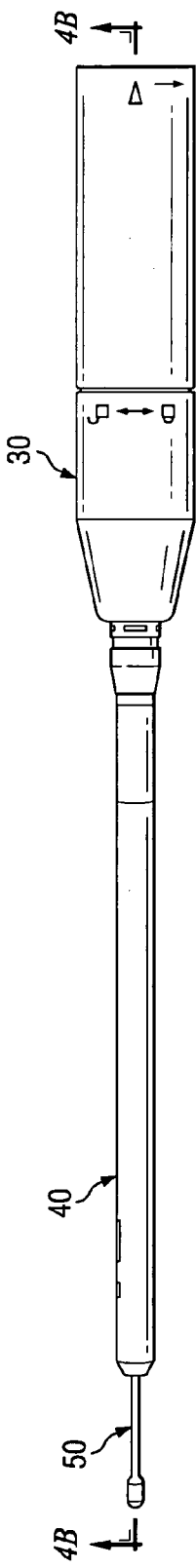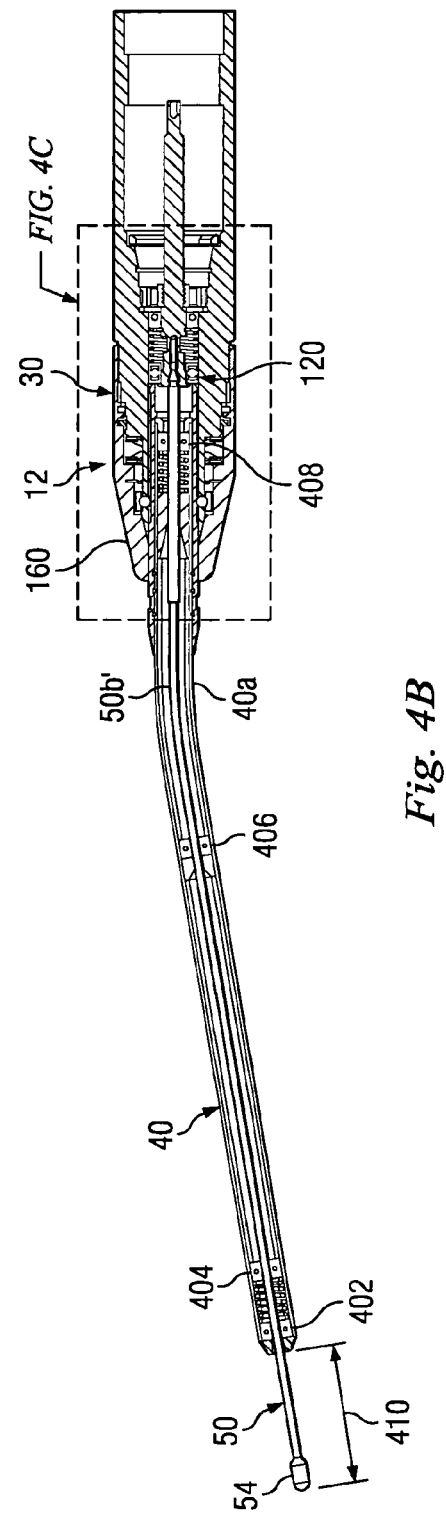

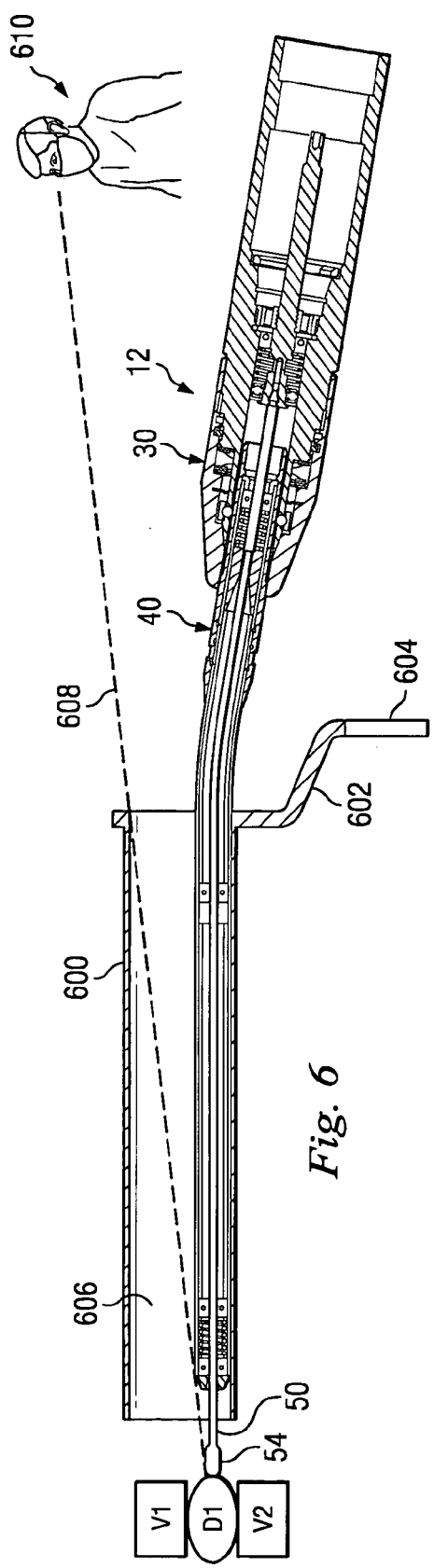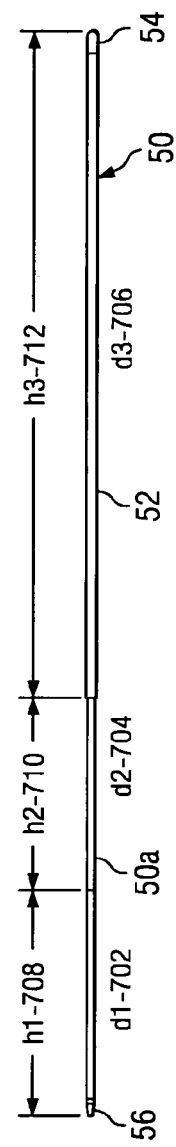
Fig. 6
Fig. 7

SURGICAL INSTRUMENT WITH ANGLED ATTACHMENT

RELATED APPLICATIONS

The present application is a continuation-in-part of copending U.S. patent application Ser. No. 10/326,178, filed on Dec. 20, 2002, which is herein incorporated by reference in its entirety.

FIELD

The present disclosure generally relates to surgical instruments for use in the dissection of bone and other tissue. More particularly, the present disclosure relates to an angled attachment for a surgical instrument.

BACKGROUND

In various surgical procedures, it is necessary to dissect bone or other tissue. Many conventional surgical instruments used for the dissection of bone or other tissue employ pneumatic or electrical motors to rotate a cutting element. In their most basic form, such surgical instruments include a motor portion having a rotary shaft, a dissection tool having a cutting or abrading element that is coupled to the rotating shaft of the motor, and a coupling arrangement for connecting the dissection tool to a spindle or collet of the rotary shaft. The spindle or collet of the rotary shaft is usually housed within a base that is attached to the motor.

Because it is frequently necessary to replace the dissection tool, a quick release coupling may be used to secure the dissection tool to the surgical instrument. An example of such a quick release coupling is shown and described in commonly assigned U.S. Pat. No. 5,505,737, which is herein incorporated by reference in its entirety. Another quick release coupling is disclosed in United States Patent Application Publication Number 2003/0023256 A1, published on Jan. 30, 2003, which is herein incorporated by reference in its entirety.

Powered surgical dissection instruments often utilize dissection tools having small shaft diameters in relation to their length. Such shafts may bend or flail in use if not adequately supported. This occurrence may be heightened when such shafts are used with motors that are designed to reach speeds in excess of 72,000 rpm. Tool makers have provided attachments or tubes that engage the motor portion and receive a portion of the dissection tool shaft. Typically, such an attachment will include one or more bearings that support the dissection tool shaft as it extends from the tool collet. Attachments may be provided with many configurations varying by length, diameter and function.

Sometimes it is desired to vary the distance between a distal end of an attachment tube and a tissue dissection head on a dissection tool. In such cases, a telescoping attachment tube may be used. An example of a telescoping attachment tube is disclosed in U.S. patent application Ser. No. 10/326, 178, filed on Dec. 20, 2002, which is herein incorporated by reference in its entirety.

A need exists in the pertinent art for an improved surgical tool which permits an angled attachment of the tool relative to the motor.

SUMMARY

In one embodiment, there is disclosed a surgical instrument for the dissection of bone or other tissue, the surgical instrument including a telescoping attachment extending at an angle with respect to a motor shaft. In an alternative aspect, the surgical instrument includes a motor having a power output; a tool having a shaft with a dissection area disposed adjacent a distal end and a coupling area disposed adjacent a proximal end; a coupling assembly configured for coupling said power output to said coupling area of said tool; and an angled attachment tube positioned along at least a portion of said shaft and substantially supporting a portion of said shaft disposed adjacent said dissection area.

Additional advantages and features of the present disclosure will become apparent from the following description and appended claims, taken in conjunction with the accompanying drawings.

Further areas of applicability of the present disclosure will become apparent from the detailed description provided hereinafter. It should be understood that the detailed description and specific examples, while indicating the several alternative embodiments, are intended for purposes of illustration only and are not intended to limit the scope of the claims.

BRIEF DESCRIPTION OF THE DRAWINGS

The present disclosure will become more fully understood from the detailed description and the accompanying drawings, wherein:

FIG. 4A is a top view of an embodiment of a telescoping surgical dissection tool.

FIGS. 4B and 4C are cross-sectional views of the embodiment of FIG. 4A in a retracted position.

FIG. 6 is a cross-sectional side view of a surgical system positioned for use in a patient.

FIG. 7 is a side view of a dissection tool.

DETAILED DESCRIPTION

The following description of several alternative embodiments is merely exemplary in nature and is in no way intended to limit the scope of the claims, or their application, or uses.

Figure 1:
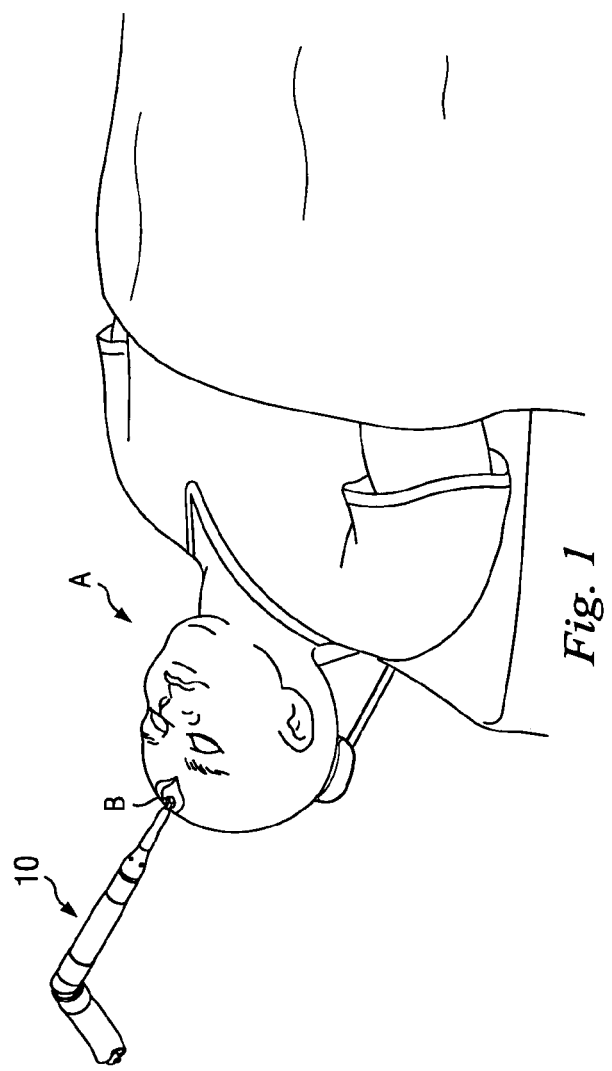
FIG. 1 is an illustration of a surgical dissection tool used in a human patient.

Referring now to FIG. 1, there is shown a human patient A undergoing a neurological operation. As is common practice, access to the brain or other neurological structures often requires delicate dissection of bone and other tissues B to gain access. By way of example, dissection tool assembly 10 in accordance with one embodiment is shown being utilized to dissect a portion of patient A's bone and other tissue B adjacent to the surgical access site.

Figure 2:
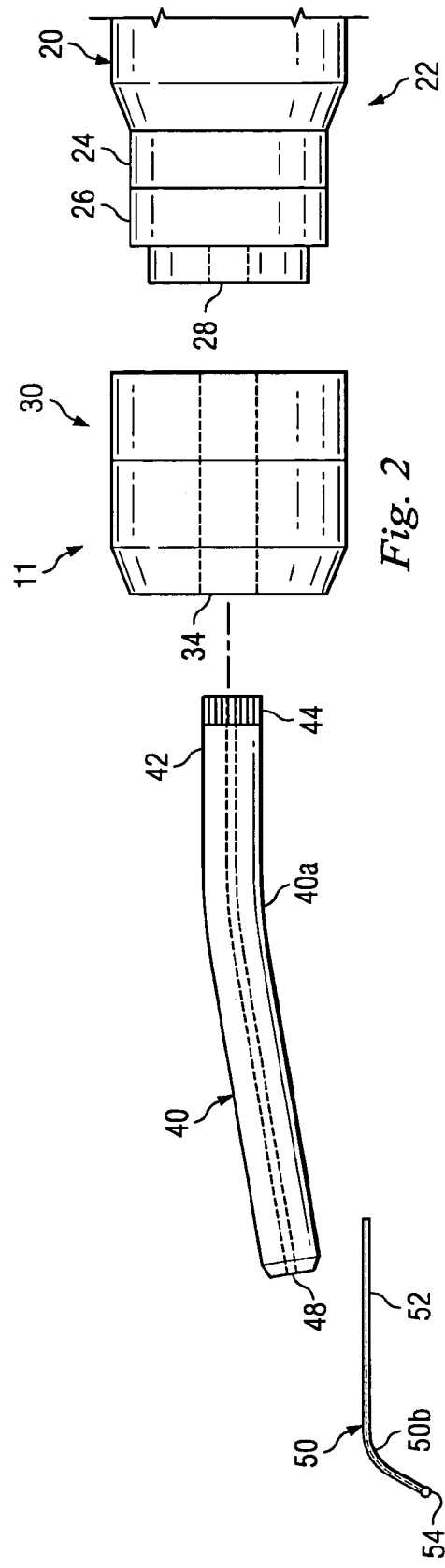
FIG. 2 is a partially exploded view of an embodiment of a surgical dissection tool.

Referring now to FIG. 2, dissection tool assembly 11 for the dissection of bone or other tissue is illustrated. Motor 20, for example a pneumatic or electric motor, is illustrated having collet assembly 22 disposed on its distal end. Collet assembly 22 will not be described in great detail in the present application as it is more fully disclosed in a prior filed application U.S. Ser. No. 10/200,683 filed Jul. 22, 2002, entitled "Surgical Instrument with Rotary Cutting Member and Quick Release Coupling Arrangement," herein incorporated by reference in its entirety. Collet assembly 22 includes proximal movable portion 24 and distal fixed portion 26. Shaft receiving aperture 28 is provided on the distal end to slidably receive a rotary shaft.

Dissection tool assembly 10 further includes attachment base coupling assembly 30 adapted to be mounted on collet assembly 22 and having attachment aperture 34 at its distal end.

Attachment tube 40 is provided having proximal portion 42 with grooves 44 extending along a portion thereof. The distal end of attachment tube 40 includes tool receiving aperture 48. Attachment tube 40 includes curved portion 40a.

Coupling assembly 30 and attachment tube 40 may be combined to form a telescoping attachment assembly. The telescoping attachment assembly will not be described in great detail in the present application as it is more fully disclosed in U.S. patent application Ser. No. 10/326,178, filed on Dec. 20, 2002, herein incorporated by reference in its entirety.

Dissection tool 50 is also shown. Dissection tool 50 includes an elongated shaft 52 and a tissue dissection head 54. As illustrated, dissection tool 50 includes curved portion 50b. In another embodiment, dissection tool 50 may be generally straight, and may only take on the illustrated curved configuration when placed within curved portion 40a of attachment tube 40.

Figure 3:
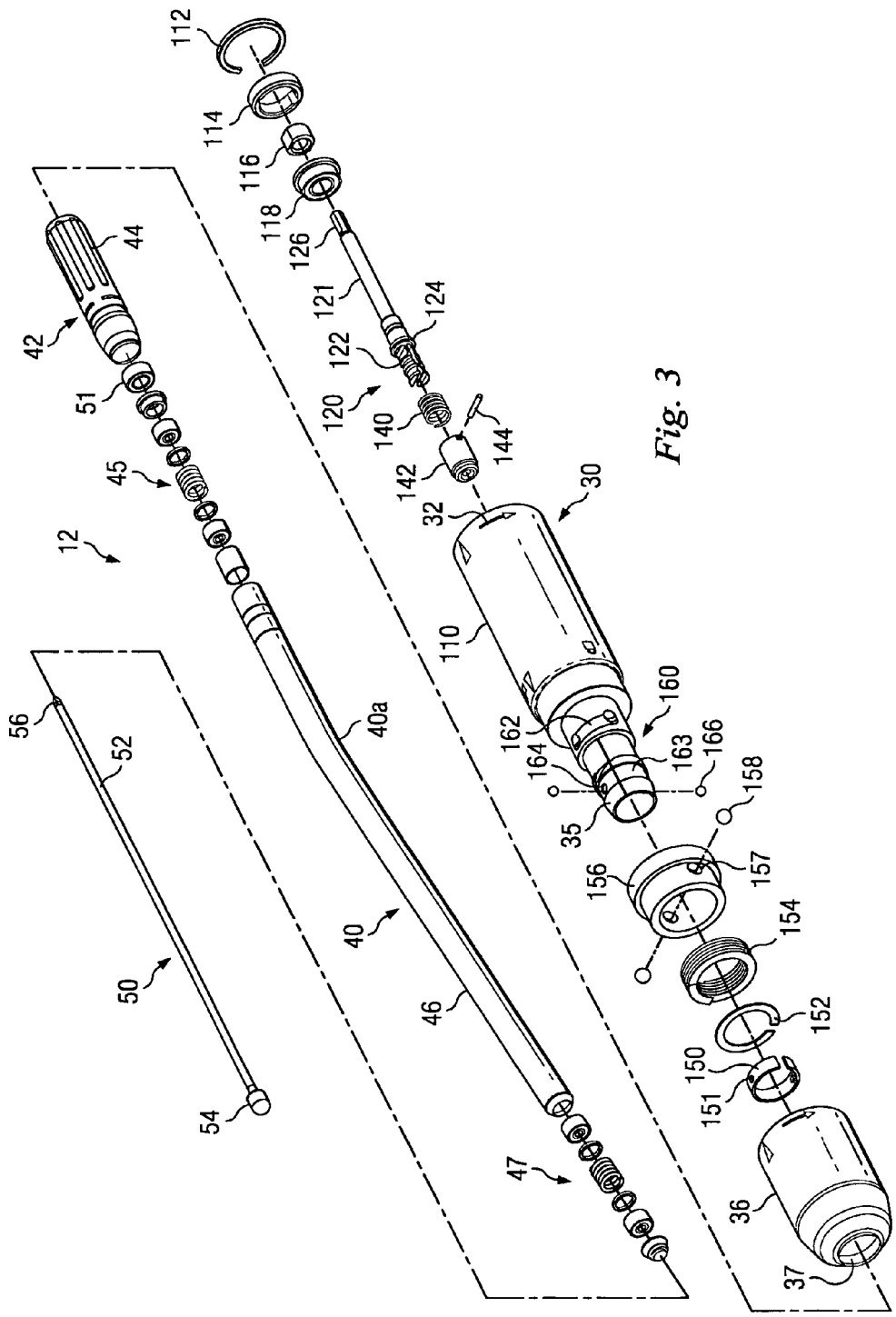
FIG. 3 is an exploded perspective view of an embodiment of a telescoping attachment assembly.

Referring now to FIG. 3, in another embodiment, there is shown an exploded perspective view of several components of an angled attachment assembly 12. Angled attachment assembly 12 includes coupling assembly 30 and attachment 40. Dissection tool 50 is also illustrated.

Attachment assembly 30 includes body 110 having an outer surface and defining an axially disposed internal passage extending substantially the length of body 110. Tool coupling assembly 120 is disposed within the internal passage.

Tool coupling assembly 120 includes split ring 112, bearing 114, retaining ring 116, bearing 118 disposed about the proximal portion of rotor shaft 121. Rotor shaft 121 includes circumferential shoulder 124 and proximal gripping end 122. Spring 140 is disposed adjacent shoulder 124 and locking sleeve 142 is circumferentially disposed about gripping end 122 and held in position by pen 144.

The distal end of coupling assembly 30 comprises attachment locking assembly 160. Attachment locking assembly 160 includes distal portion 36, tension ring 150 having apertures 151 disposed therein, split ring 152, spring 154, collar 156 having apertures 157 and locking ball 158 disposed therein. Balls 166 are disposed within apertures 151 in their assembled condition and similarly extend through apertures 164 disposed in body 110. Body 110 further defines collet fingers 163 at its distal extreme. Helical groove 162 is provided to receive locking balls 158. Helical groove 162 further includes shallow detents at either end of its length. It will be understood that these shallow detents provide a provisional locking of the locking balls when they reach this position, thereby maintaining the assembly in the select position. This may also provide the user with tactile feedback as the balls fall into the detents.

Attachment tube 40 includes proximal portion 42 having a plurality of axially aligned grooves 44 disposed on the exterior surface. Proximal bearing assembly 45 is shown having a number of bearings, rings and a tension spring illustrated therebetween. Bearing 51 is disposed proximally of proximal bearing assembly 45. Attachment tube 40 also includes distal bearing assembly 47.

Angled portion 40a is shown adjacent distal bearing assembly 47. In another embodiment, angled portion 40a may be in the middle of attachment tube 40, or adjacent proximal bearing assembly 45. Proximal bearing assembly 45 and distal bearing assembly 47 are fixably disposed within tube 46 and are preferably adapted to support an angled rotating shaft. Proximal portion 42 is fixably attached to the exterior of tube 46 and retains bearing 51 in position.

Dissection tool 50 is also shown. Dissection tool 50 includes elongated shaft 52, tissue dissection head 54, and attachment mechanism 56. As illustrated, dissection tool 50 is substantially straight. In another embodiment, dissection tool 50 may take on a curved configuration when placed within curved portion 40a of attachment tube 40.

Figure 4C:
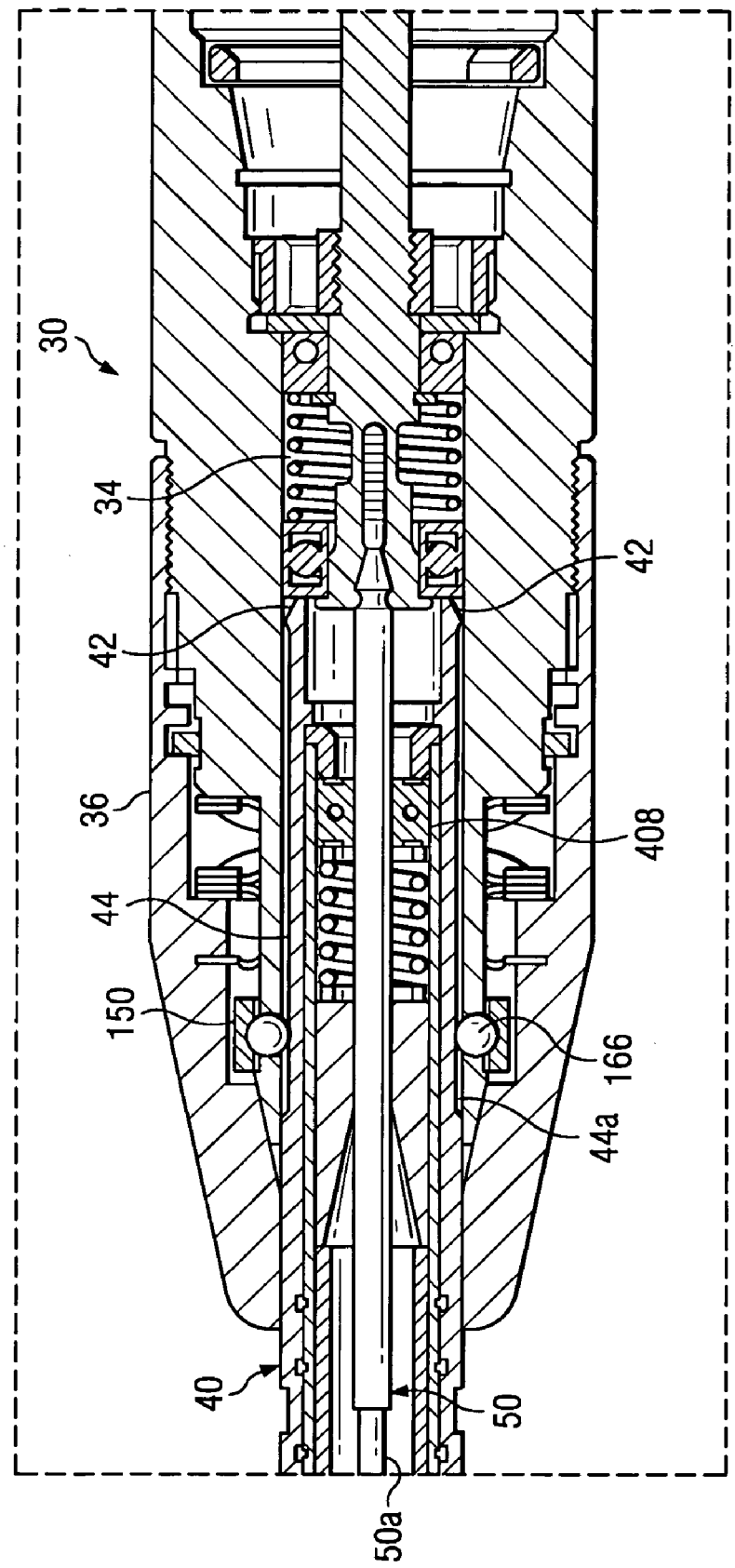

Referring now to FIGS. 4A through 4C, another embodiment of tool coupling assembly 120 and attachment or locking assembly 160 will be more fully described. Cross-sectional view of FIGS. 4B and 4C show telescoping attachment assembly 12 and tube 40 in the fully retracted position. Dissection tool 50 is locked within tool coupling assembly 120 and attachment tube 40 is retracted within attachment locking assembly 160. Tube 40 has an angled and/or curved portion 40a. Angled and/or curved portion 40a may have an angle of about 10° and/or radius of curvature of about 2 inches. Dissection tool 50 extends within tube 40 and has bend 50b' adjacent curved portion 40a.

As shown more fully in FIG. 4C, proximal portion 42 of attachment tube 40 extends within internal chamber 34 of coupling assembly 30. Ball 166 is disposed within groove 44 and is retained in this position by tension ring 150. As shown, ball 166 is approaching distal end 44a of groove 44, so that distance 410 between distal end of tube 40 and dissection head 54 is maximized. In one embodiment, distance 410 is between about 0.25 and 0.75 inches, for example about 0.5 inches. Dissection tool 50 is supported within attachment tube 40 by bearings 402, 404, 406, and/or 408. Dissection tool 50 includes reduced diameter portion 50a, which will be more fully discussed below.

In one embodiment, dissection tool 50 remains axially stationary relative to coupling assembly 30, while tube 40 is axially movable, for example telescoping, with respect to coupling assembly 30.

Other details of dissection tool 50 will not be presented here as they are more fully disclosed in one or more of the incorporated references and/or known by those skilled in the art.

Figure 5A:
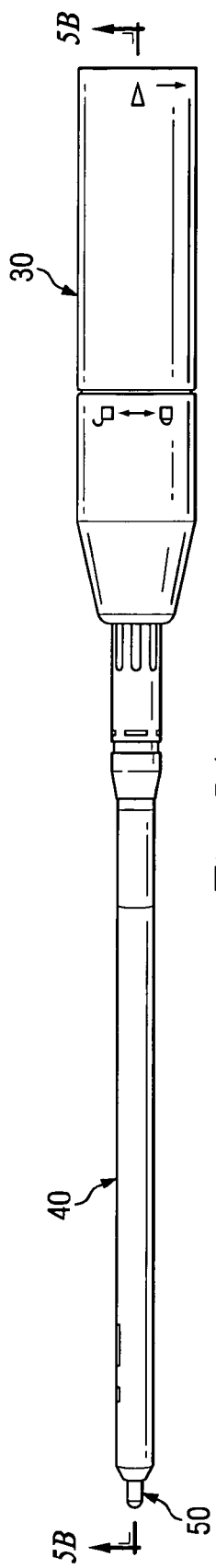
FIG. 5A is a top view of an embodiment of a telescoping surgical dissection tool.
Figure 5B:
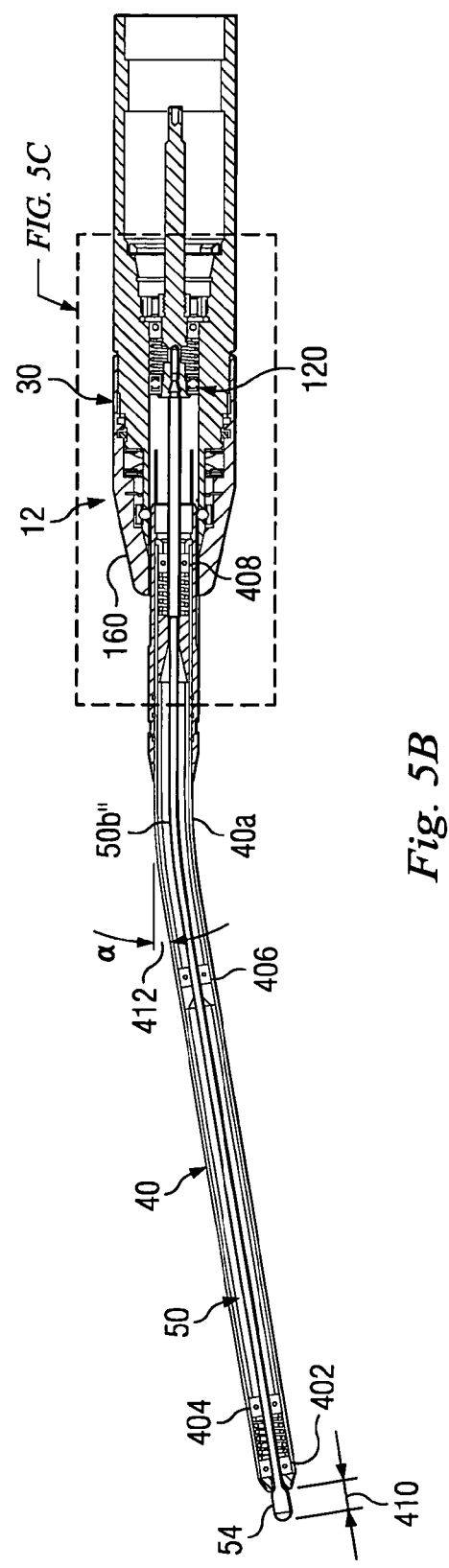
FIGS. 5B and 5C are cross-sectional views of the embodiment of FIG. 5A in an extended position.
Figure 5C:
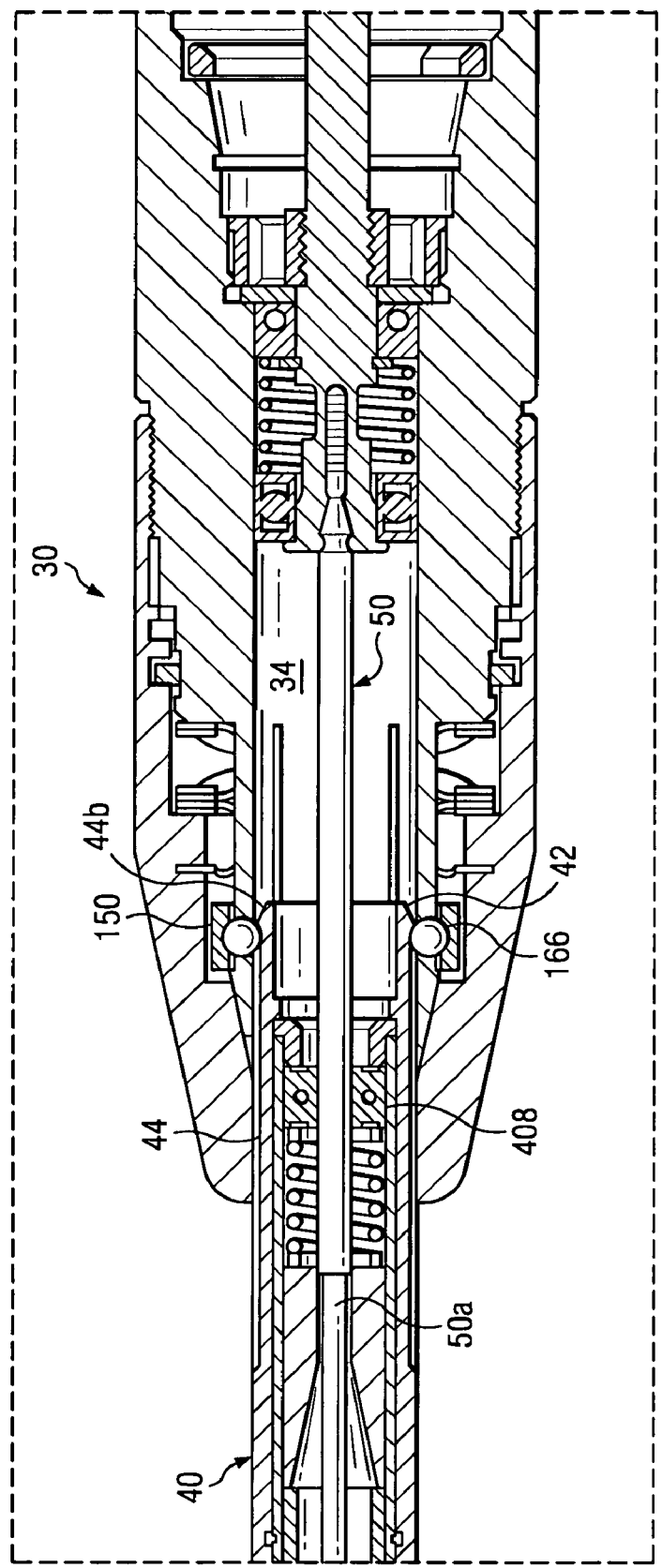

Referring now to FIGS. 5A through 5C, another embodiment of tool coupling assembly 120 and attachment or locking assembly 160 will be more fully described. Cross-sectional view of FIGS. 5B and 5C show telescoping attachment assembly 12 and tube 40 in the fully extended position. Dissection tool 50 is locked within tool coupling assembly 120 and attachment tube 40 is extending out of attachment or locking assembly 160. In this configuration, dissection tool 50 has bend 50b" corresponding to the new location of curved portion 40a along the shaft of dissection tool 50.

As shown more fully in FIG. 5C, proximal portion 42 of attachment tube 40 extends within internal chamber 34 of coupling assembly 30. Ball 166 is disposed within groove 44 and is retained in this position by tension ring 150. As shown, ball 166 is approaching proximal end 44b of groove 44, so that distance 410 between distal end of tube 40 and dissection head 54 is minimized. In one embodiment, distance 410 is between about 0.0 and 0.25 inches, for example about 0.1 inches. Dissection tool 50 is supported within attachment tube 40 by bearings 402, 404, 406, and/or 408. Dissection tool 50 includes reduced diameter portion 50a, which will be more fully discussed below.

Tube 40 has an offset angle α 412, or the bend angle of tube 40 from its proximal to distal ends. In one embodiment, offset angle α 412 is between about 3° and 30°. In another embodiment, offset angle α 412 is between about 5° and 20°. In another embodiment, offset angle α 412 is between about 7.5° and 15°. In another embodiment, offset angle α 412 is about 10°.

Other details of dissection tool 50 will not be presented here as they are more fully disclosed in one or more of the incorporated references and/or known by those skilled in the art.

Referring now to FIG. 6, there is illustrated another embodiment of angled attachment assembly 12 within viewing tube 600, for example an endoscopic tube or a microscopic tube. Angled attachment assembly 12 includes coupling assembly 30, angled attachment 40, and angled dissection tool 50. Tube 600 includes handle 602, and attachment mechanism 604 at the distal end of the handle 602, for example for attaching handle 602 to a frame, or to hold handle 602 with a hand. Tube 600 includes aperture 606 having a larger diameter than attachment 40, for example about 2 times to about 5 times the diameter. Aperture 606 enables a line of sight 608 from dissection head 54 to physician 610, so that physician 610 can see dissection head 54 and/or the tissue that dissection head 54 is encountering.

Although angled attachment assembly 12 and viewing tube 600 have many other applications, as illustrated, viewing tube 600 is shown adjacent vertebral bodies V1 and V2 having an intervening disk space D1. With use of angled attachment assembly 12 and viewing tube 600, physician 610 may view disk space D1 and surrounding tissues while a portion of attachment 40 is located within aperture 606.

Referring now to FIG. 7, there is illustrated another embodiment of dissection tool 50. Dissection tool 50 includes elongated shaft 52, tissue dissection or cutting head 54, and attachment mechanism 56. As illustrated, dissection tool 50 includes reduced diameter portion 50a. In another embodiment, dissection tool 50 has a substantially constant outer diameter.

In one embodiment, dissection tool 50 has a total height of h1—708, plus h2—710, plus h3—712, of about 1 to about 6 inches. In another embodiment, h1—708 is between about 0.1 and 1.5 inches. In another embodiment, h2—710 is between about 0.05 and 0.5 inches. In another embodiment, h3—712 is between about 0.25 and about 5 inches.

In one embodiment, each of diameters d1—702, d2—704, and d3—706 are between about 0.02 and 0.5 inches. In another embodiment, diameters d1—702, d2—704, and d3—706 are between about 0.03 and 0.1 inches. In another embodiment, diameters d1—702 and d3—706 are substantially the same, for example about 0.047 inches, and diameter d2—704 is less than diameters d1—702 and d3—706, for example about 0.038 inches. In another embodiment, diameter d2—704 is between about 0.001 and 0.1 inches less than diameters d1—702 and/or d3—706.

In one embodiment, there is disclosed a surgical instrument for the dissection of bone or other tissue, the surgical instrument including a motor having a power output; a tool having a shaft with a dissection area disposed adjacent a distal end and a coupling area disposed adjacent a proximal end; a coupling assembly configured for coupling said power output to said coupling area of said tool; and an angled attachment tube positioned along at least a portion of said shaft and substantially supporting a portion of said shaft disposed adjacent said dissection area. In another embodiment, the coupling assembly has a longitudinal axis and said angled attachment tube is movable along said longitudinal axis. In another embodiment, the attachment tube is configured such that movement along said longitudinal axis is accomplished without substantial rotary motion. In another embodiment, the attachment tube is movably coupled to said coupling assembly. In one aspect, the attachment tube is movably coupled to said coupling assembly to permit telescoping adjustment therebetween; a dissection tool may be fixedly coupled to the coupling assembly such that any curves in the attachment to create corresponding curves in the tool shaft at variable positions along the tool's length. In another embodiment, the surgical instrument also includes a second coupling assembly linked to said coupling assembly, said second coupling assembly adapted to selectively lock said attachment tube to said coupling assembly. In another embodiment, the second coupling assembly includes a locked position wherein said attachment tube is locked to said coupling assembly, a guiding position wherein said attachment tube is moveably coupled to said coupling assembly, and an open position wherein said attachment tube is removed from said coupling assembly. In another embodiment, the coupling assembly and said attachment tube include a projection and detent retention system therebetween to retain said attachment tube in said guiding position. In another embodiment, the attachment tube defines a plurality of elongated detents along an outer surface and said coupling assembly includes at least one projection for mating with said elongated detents. In another embodiment, the at least one projection may be slidably disposed in said elongated detents to permit axial movement of said attachment tube with respect to said coupling assembly. In another embodiment, the coupling assembly includes an aperture for receiving said attachment tube and at least one movable projection extending into said aperture, wherein said movable projection cooperates with said attachment tube to retain said attachment tube in the guiding position. In another embodiment, the movable projection provides a tactile sensation to the user to indicate movement between the open position and the guiding position. In another embodiment, the motor includes a motor housing and said coupling assembly is removably coupled to said motor housing. In another embodiment, the motor housing includes a tool chuck and said coupling assembly includes a work shaft, said work shaft removably coupled to said tool chuck. In another embodiment, the tool chuck is moved to a locked position coupling the work shaft by rotational movement of said coupling assembly about a portion of said motor housing. In another embodiment, the angled attachment tube includes a curved portion. In another embodiment, the attachment tube further comprises at least one bearing proximal to the curved portion and at least one bearing distal to the curved portion to support at least a portion of the shaft. In another embodiment, the shaft includes a reduced diameter portion. In another embodiment, the shaft includes a curved portion. In another embodiment, the angled attachment tube has an angle of between about 3° and about 30°. In another embodiment, the tool has a height of about 1 to about 6 inches. In another embodiment, the tool has a diameter of about 0.02 to about 0.5 inches.

In one embodiment, there is disclosed a method of assembling a surgical dissection instrument, including providing a motor with a first tool chuck, a dissection tool, and a coupler with a work shaft and a second tool chuck, and an angled attachment; attaching the coupler to the motor with the work shaft coupled to the first tool chuck; joining the angled attachment to the coupler; inserting a portion of the dissection tool through the angled attachment and into the second tool chuck; and locking the dissection tool in the second tool chuck. In another embodiment, the joining permits axial displacement of the angled attachment with respect to the coupler and further including, adjusting the axial displacement of the angled attachment with respect to the coupler and locking the coupler to the angled attachment. In another embodiment, the method also includes moving the angled attachment with respect to the coupler to unlock the dissection tool from the second tool chuck and removing the dissection tool from the angled attachment.

In one embodiment, there is disclosed a telescoping attachment assembly for use with a surgical dissection tool, including an angled attachment having an outer surface and defining an internal bore for receiving the surgical dissection tool, said angled attachment having a proximal end; a coupler having a distal aperture for telescoping engagement said proximal end, said coupler including a first locking mechanism disposed adjacent to said aperture for selectively locking said angled attachment to said coupler, and said coupler including a second locking mechanism for selectively locking the surgical dissection tool to said coupler. In another embodiment, the coupler is adapted for connection to a powered surgical handpiece. In another embodiment, the coupler is adapted for removable connection to a powered surgical handpiece.

In one embodiment, there is disclosed a surgical system including a surgical instrument comprising a motor having a power output; a tool having a shaft with a dissection area disposed adjacent a distal end and a coupling area disposed adjacent a proximal end; a coupling assembly configured for coupling said power output to said coupling area of said tool; and an angled attachment tube positioned along at least a portion of said shaft and substantially supporting a portion of said shaft disposed adjacent said dissection area; and a viewing tube adapted to receive at least a distal portion of the surgical instrument. In another embodiment, the attachment tube includes a curved portion. In another embodiment, the attachment tube further comprises at least one bearing proximal to the curved portion and at least one bearing distal to the curved portion to support the portion of the shaft. In another embodiment, the shaft includes a reduced diameter portion. In another embodiment, the shaft includes a curved portion. In another embodiment, the angled attachment tube has an angle of between about 3° and about 30°. In another embodiment, the tool has a height of about 1 to about 6 inches. In another embodiment, the tool has a diameter of about 0.02 to about 0.5 inches. In another embodiment, the viewing tube further comprises a handle. In another embodiment, the viewing tube comprises a first diameter, and wherein said angled attachment tube comprises a second diameter, further wherein the first diameter is at least about two times the second diameter.

The above description has been directed to various embodiments of coupling assemblies (30) that are detachable from their respective motors (20), however; in another embodiment, that a coupler may be integrated with a motor in a substantially integral unit (not shown). It is understood that dissection tool 50 may have sufficient flexibility to conform to the curvature of the attachment along its length.

The above-described embodiments of the present disclosure may be assembled and adjusted by manual manipulation of the outer surfaces of the components.

The above-described embodiments of the present disclosure include a number of reference numerals provided to aid in the understanding of the disclosed devices. Although the same reference numerals have been used in multiple figures and for multiple embodiments for the sake of convenience, it should not be assumed that the same reference numeral refers to the same element or that similarly numbered elements are the same element in each of the figures and embodiments.

The above description of the embodiments according to the disclosure are merely exemplary in nature and, thus, variations that do not depart from the gist of the invention are intended to be within the scope of the invention. Such variations are not to be regarded as a departure from the spirit and scope of the invention.

What is claimed is:

1. A surgical instrument for the dissection of bone or other tissue having a motor with a power output, the surgical instrument comprising:
    a dissection tool having an elongated shaft, a proximal end, and a distal end;
    a coupling assembly for coupling the power output to the proximal end of the dissection tool, the coupling assembly extending along a longitudinal axis;
    an attachment tube having a proximal portion movably coupled to the coupling assembly and an internal passage extending from the proximal portion to an opposite distal portion, the proximal portion of the internal passage extending substantially along the longitudinal axis and the distal portion of the internal passage extending at an oblique angle with respect to the longitudinal axis; and
    a locking assembly movably coupled to the coupling assembly, the locking assembly movable between a locked position wherein the attachment tube is locked to the coupling assembly, a guiding position wherein the attachment tube is moveably coupled to the coupling assembly, and an open position wherein the attachment tube is removable from the coupling assembly,
    wherein the attachment tube is movable along the longitudinal axis between a first coupled position and a second coupled position with respect to the coupling assembly such that the distal end of the dissection tool extends beyond the distal portion of the attachment tube a first distance in the first coupled position and the distal end of the dissection tool extends beyond the distal portion of the attachment tube a second distance in the second coupled position, wherein the second distance is greater than the first distance.

2. The surgical instrument of claim 1, wherein the attachment tube is couplable to the coupling assembly at a plurality of locations along the longitudinal axis with respect to the coupling assembly.

3. The surgical instrument of claim 1, wherein the coupling assembly and the attachment tube are movably coupled to one another in the guiding position via a projection and detent retention system.

4. The surgical instrument of claim 3, wherein the attachment tube comprises an outer surface with at least one elongated detent and the coupling assembly comprises at least one projection for mating with the at least one elongated detent.

5. The surgical instrument of claim 4, wherein the at least one projection slidably engages the at least one elongated detent to permit movement of the attachment tube along the longitudinal axis with respect to the coupling assembly.

6. The surgical instrument of claim 1, wherein the attachment tube further comprises at least one bearing in the proximal portion and at least one bearing in the distal portion, each of the bearings supporting at least a portion of the elongated shaft.

7. The surgical instrument of claim 1, wherein the attachment tube further comprises a curved transition portion connecting the proximal portion of the attachment tube to the distal portion of the attachment tube.

8. The surgical instrument of claim 1, wherein the distal portion of the internal passage extends along an axis at an oblique angle of between about 3° and about 30° with respect to the longitudinal axis.

9. A surgical instrument for the dissection of bone or other tissue having a motor with a power output, the surgical instrument comprising:
   a dissection tool having an elongated shaft, a coupling area adjacent a proximal portion, and a dissecting area adjacent a distal portion;
   a coupling assembly for fixedly coupling the power output to the coupling area of the dissection tool, the coupling assembly extending along a longitudinal axis;
   an attachment tube movably coupled to the coupling assembly, the attachment tube receiving and supporting at least a portion of the elongated shaft, a proximal portion of the attachment tube extending substantially along the longitudinal axis and a distal portion of the tube extending along an axis extending at an oblique angle with respect to the longitudinal axis, a curved transition portion connecting the proximal portion to the distal portion; and
   a locking assembly movably coupled to the coupling assembly, the locking assembly movable between a locked position wherein the attachment tube is locked to the coupling assembly, a guiding position wherein the attachment tube is moveably coupled to the coupling assembly, and an open position wherein the attachment tube is removable from the coupling assembly,
   wherein the attachment tube is movable along the longitudinal axis with respect to the coupling assembly between a first coupled position and a second coupled position,
   wherein in the first coupled position the elongated shaft of the dissection tool includes a bend corresponding to the curved transition portion of the attachment tube at a first distance from the dissecting area, and
   wherein in the second coupled position the elongated shaft of the dissection tool includes a bend corresponding to the curved transition portion of the attachment tube at a second distance from the dissecting area, the second distance being less than the first distance.

10. The surgical instrument of claim 9, wherein the attachment tube is couplable to the coupling assembly at a plurality of locations along the longitudinal axis.

11. The surgical instrument of claim 9, wherein the coupling assembly includes an aperture for receiving the attachment tube and at least one movable projection extends into the aperture, wherein in the guiding position the at least one movable projection movably engages a recess of the attachment tube to retain the attachment tube in the guiding position.

12. The surgical instrument of claim 11, wherein the at least one movable projection provides a tactile sensation to the user to indicate movement between the guiding position and the open position.

13. The surgical instrument of claim 11, wherein the axis of the distal portion of the attachment tube extends at an oblique angle of between about 3° and about 30° with respect to the longitudinal axis.

14. The surgical instrument of claim 9, wherein the motor includes a motor housing and the coupling assembly is removably coupled to the motor housing.

15. The surgical instrument of claim 9, wherein the attachment tube further comprises at least one bearing in the proximal portion and at least one bearing in the distal portion, each of the bearings supporting at least a portion of the elongated shaft.

16. A surgical instrument for the dissection of bone or other tissue having a motor with a power output, the surgical instrument comprising:
   a dissection tool having an elongated shaft, a coupling area adjacent a proximal end, and a dissecting area adjacent a distal end;
   a coupling assembly for fixedly coupling the power output to the coupling area of the dissection tool, the coupling assembly extending along a longitudinal axis; and
   an attachment tube movably coupled to the coupling assembly, the attachment tube receiving and supporting at least a portion of the elongated shaft, a proximal portion of the tube extending substantially along the longitudinal axis and a distal portion of the tube extending along an axis extending at an oblique angle with respect to the longitudinal axis, a curved transition portion connecting the proximal portion to the distal portion;
   wherein the attachment tube is movable along the longitudinal axis between a first coupled position and a second coupled position with respect to the coupling assembly;
   wherein the distal end of the dissection tool extends beyond the distal portion of the attachment tube a first distance in the first coupled position and the distal end of the dissection tool extends beyond the distal portion of the attachment tube a second distance in the second coupled position, wherein the second distance is less than the first distance;
   wherein in the first coupled position the elongated shaft of the dissection tool includes a bend corresponding to the curved transition portion of the attachment tube at a third distance from the dissecting area; and
   wherein in the second coupled position the elongated shaft of the dissection tool includes a bend corresponding to the curved transition portion of the attachment tube at a fourth distance from the dissecting area, the fourth distance being less than the third distance.

17. The surgical instrument of claim 16, wherein the attachment tube is couplable to the coupling assembly at a plurality of locations along the longitudinal axis.

18. The surgical instrument of claim 16, wherein the attachment tube further comprises at least one bearing in the proximal portion and at least one bearing in the distal portion, each of the bearings for supporting at least a portion of the elongated shaft.

* * * * *